US012310426B2

(12) United States Patent
Molard et al.

(10) Patent No.: US 12,310,426 B2
(45) Date of Patent: May 27, 2025

(54) TEXTILE DEVICE FOR PREGNANT WOMEN

(71) Applicant: LABORATOIRES INNOTHERA, Arcueil (FR)

(72) Inventors: Nathanaël Molard, Arcueil (FR); Marylène Jeandel, Arcueil (FR); Olivier Mailliot, Arcueil (FR)

(73) Assignee: LABORATOIRES INNOTHERA, Arcueil (FR)

( * ) Notice: Subject to any disclaimer, the term of this patent is extended or adjusted under 35 U.S.C. 154(b) by 72 days.

(21) Appl. No.: 17/679,264

(22) Filed: Feb. 24, 2022

(65) Prior Publication Data

US 2022/0279866 A1 Sep. 8, 2022

(30) Foreign Application Priority Data

Mar. 5, 2021 (FR) ........................................ 2102139

(51) Int. Cl.
 *A41C 1/10* (2006.01)
(52) U.S. Cl.
 CPC ....................................... *A41C 1/10* (2013.01)
(58) Field of Classification Search
 USPC ........................................ 450/131, 132, 155
 See application file for complete search history.

(56) References Cited

U.S. PATENT DOCUMENTS

| 1,469,069 | A | * | 9/1923 | Freedenberg | ............. | A61F 5/03 |
| | | | | | | 450/114 |
| 2,862,500 | A | * | 12/1958 | Blatt | ........................ | A41C 1/10 |
| | | | | | | D2/625 |
| 5,060,639 | A | * | 10/1991 | Marcus | .................... | A61F 5/028 |
| | | | | | | 128/95.1 |
| D328,383 | S | * | 8/1992 | Working, Jr. | ................. | D29/100 |
| 5,613,893 | A | * | 3/1997 | Zagame | ..................... | A41C 1/10 |
| | | | | | | 2/311 |
| 5,690,122 | A | * | 11/1997 | Weber-Unger | ........... | A41C 1/10 |
| | | | | | | 602/19 |
| 6,071,175 | A | * | 6/2000 | Working, III | ............. | A41C 1/10 |
| | | | | | | 2/45 |
| D437,416 | S | * | 2/2001 | Slautterback | ................. | D24/190 |
| 11,213,082 | B1 | * | 1/2022 | Yang | ........................ | A41D 1/08 |

(Continued)

FOREIGN PATENT DOCUMENTS

FR   3 072 871 A1  5/2019
WO  2020/035204 A1  2/2020

*Primary Examiner* — Jocelyn Bravo
(74) *Attorney, Agent, or Firm* — Oliff PLC

(57) ABSTRACT

A device having an elastic ventral band having a right-hand ventral portion and a left-hand ventral portion that are intended to extend respectively on the right-hand side and the left-hand side of the pregnant woman's belly in a use position in which said device is being worn by the pregnant woman, and a dorsal band having a right-hand dorsal portion and a left-hand dorsal portion that are intended to extend respectively on the right-hand side and the left-hand side of the pregnant woman's back in said use position, the device being characterized in that, when it is seen flat in a side view, the axis ($D_{34d}$, $D_{34g}$) of at least one of the right-hand and left-hand ventral portions is inclined, with respect to a transverse plane, at an angle greater than 5° and less than 80°.

14 Claims, 5 Drawing Sheets

(56) References Cited

U.S. PATENT DOCUMENTS

| | | | |
|---|---|---|---|
| 2005/0136798 A1* | 6/2005 | Jennings | A61F 13/148 |
| | | | 450/155 |
| 2007/0033696 A1* | 2/2007 | Sellier | A61H 7/001 |
| | | | 2/69 |
| 2015/0245951 A1* | 9/2015 | Convert | D04B 1/106 |
| | | | 66/107 |
| 2018/0007977 A1* | 1/2018 | Windenberger | A41C 1/10 |
| 2020/0260805 A1* | 8/2020 | Ovington | A41D 17/02 |

* cited by examiner

[Fig 1]
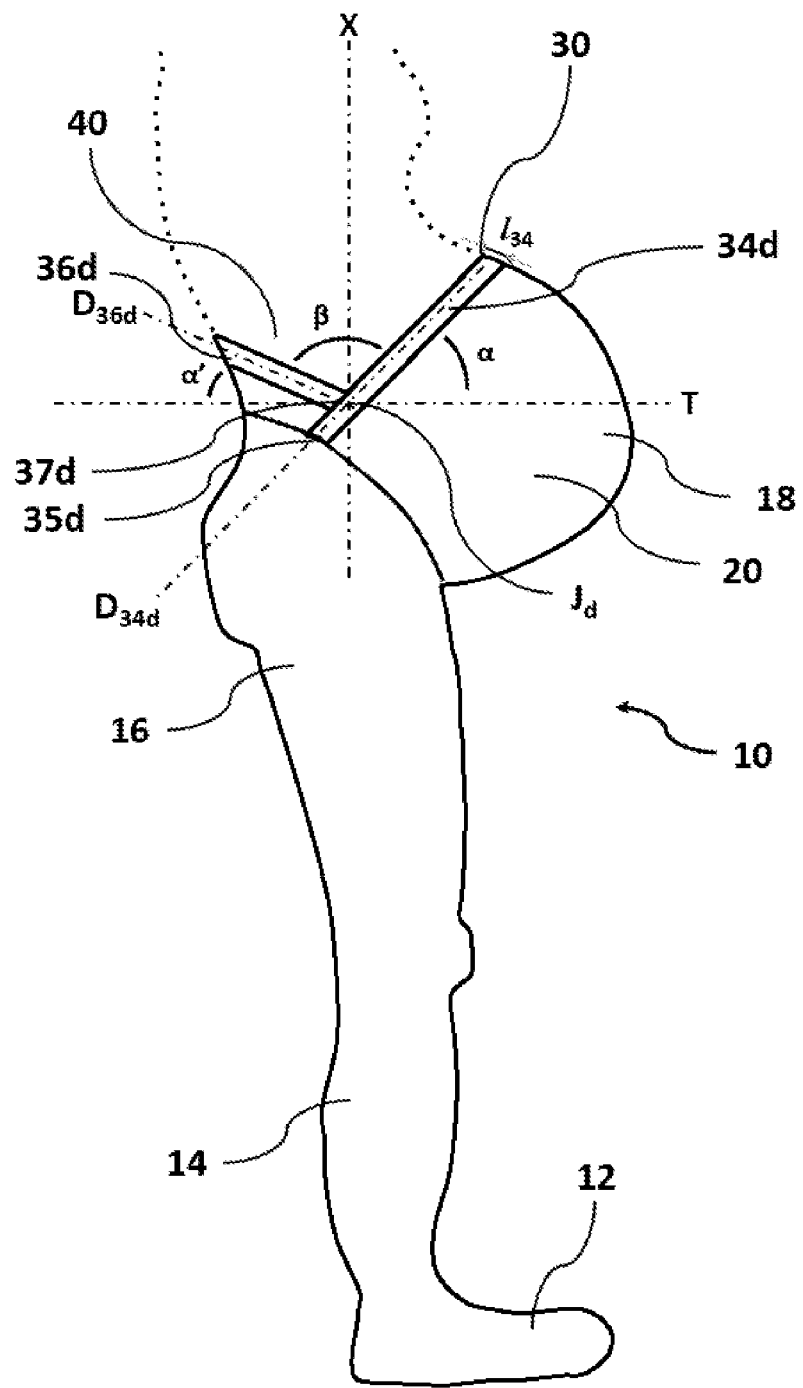

[Fig 2]
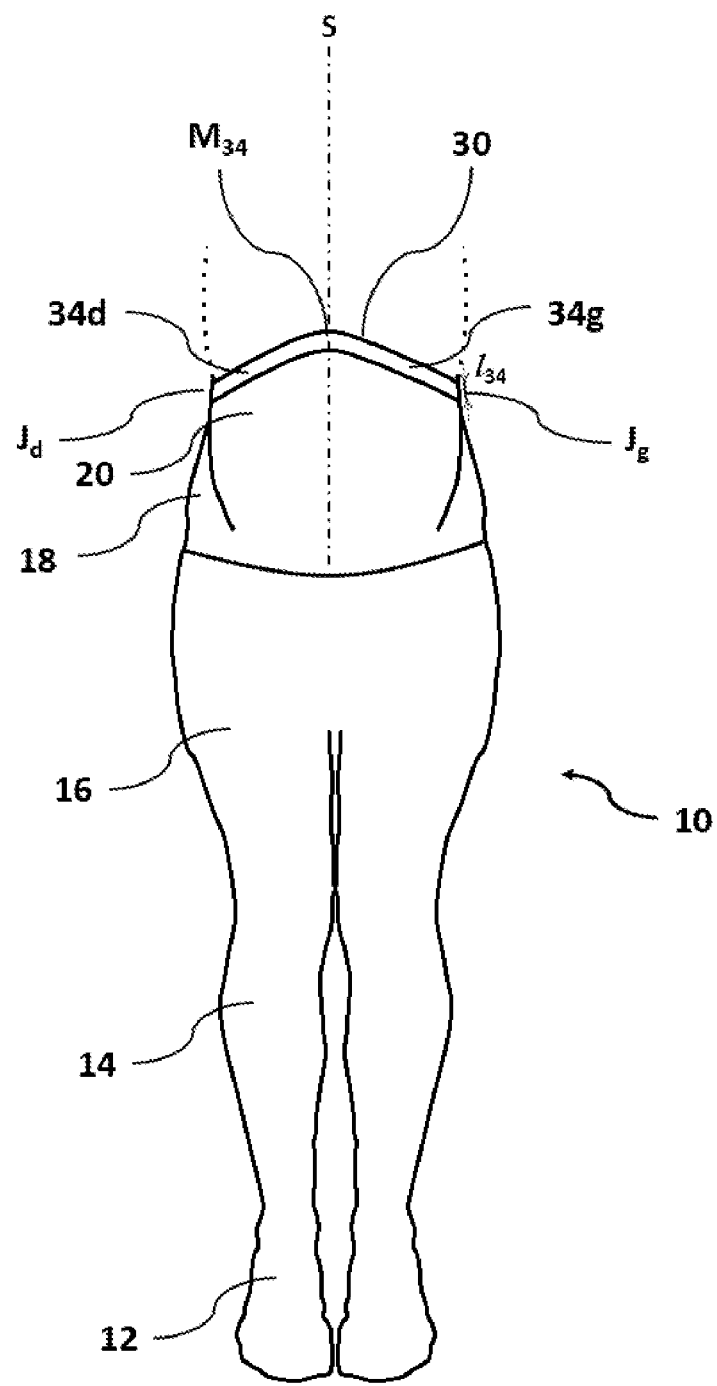

[Fig 3]
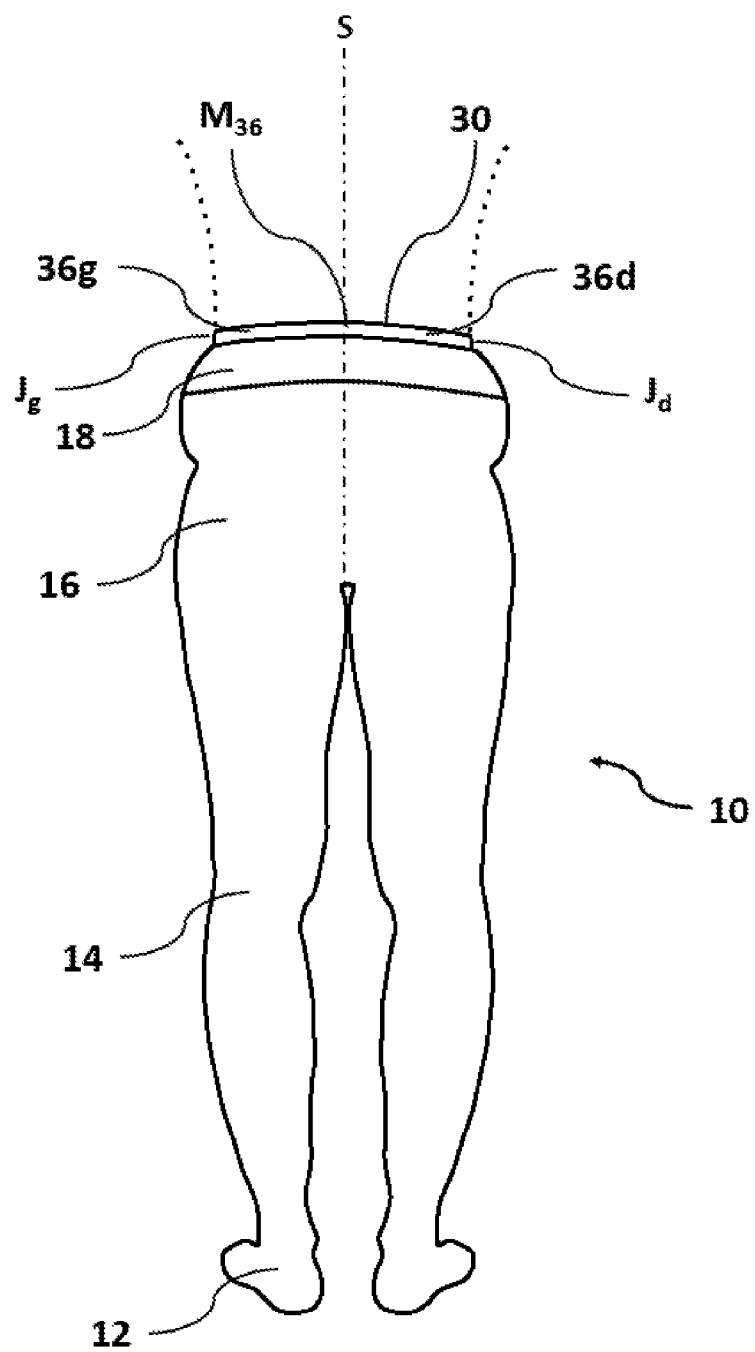

[Fig 4]
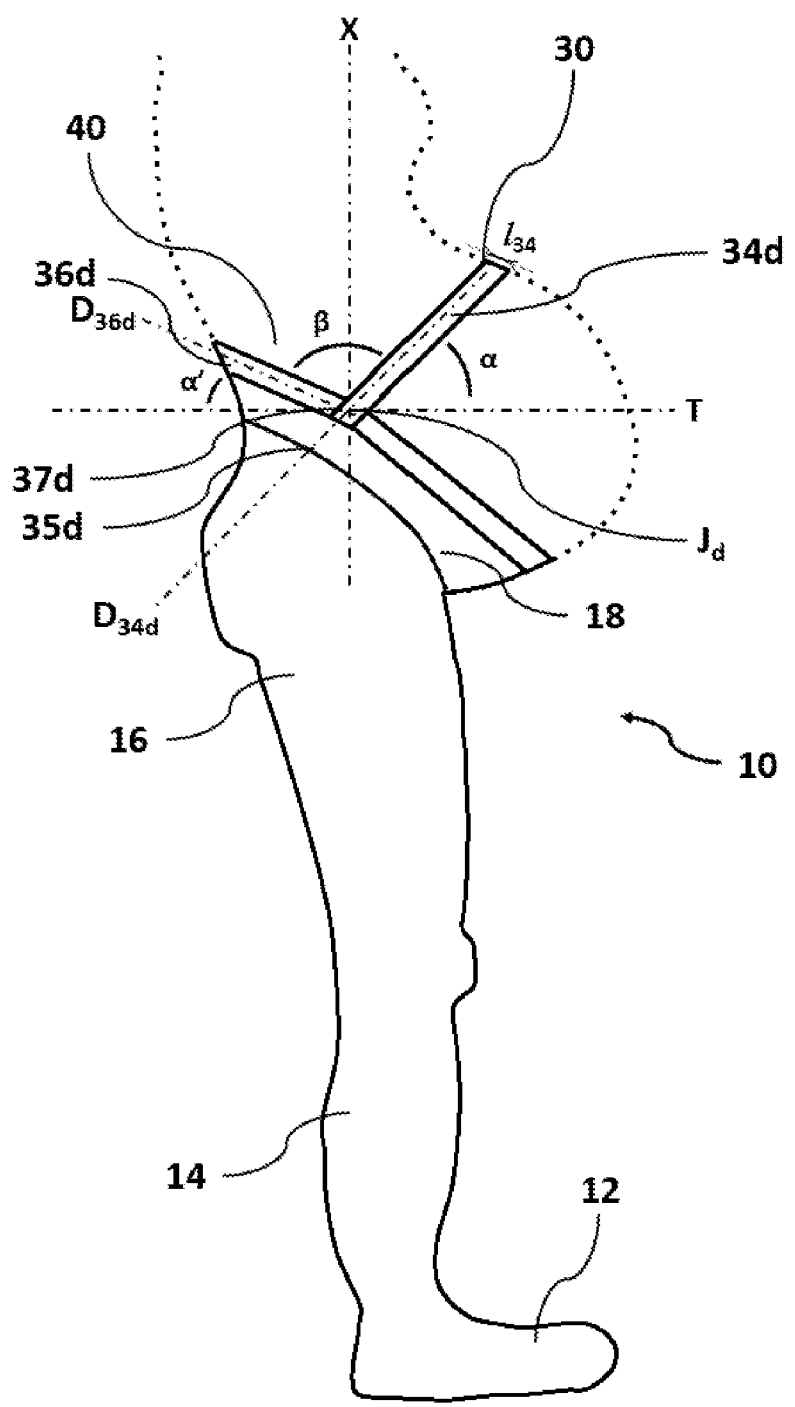

[Fig 5]
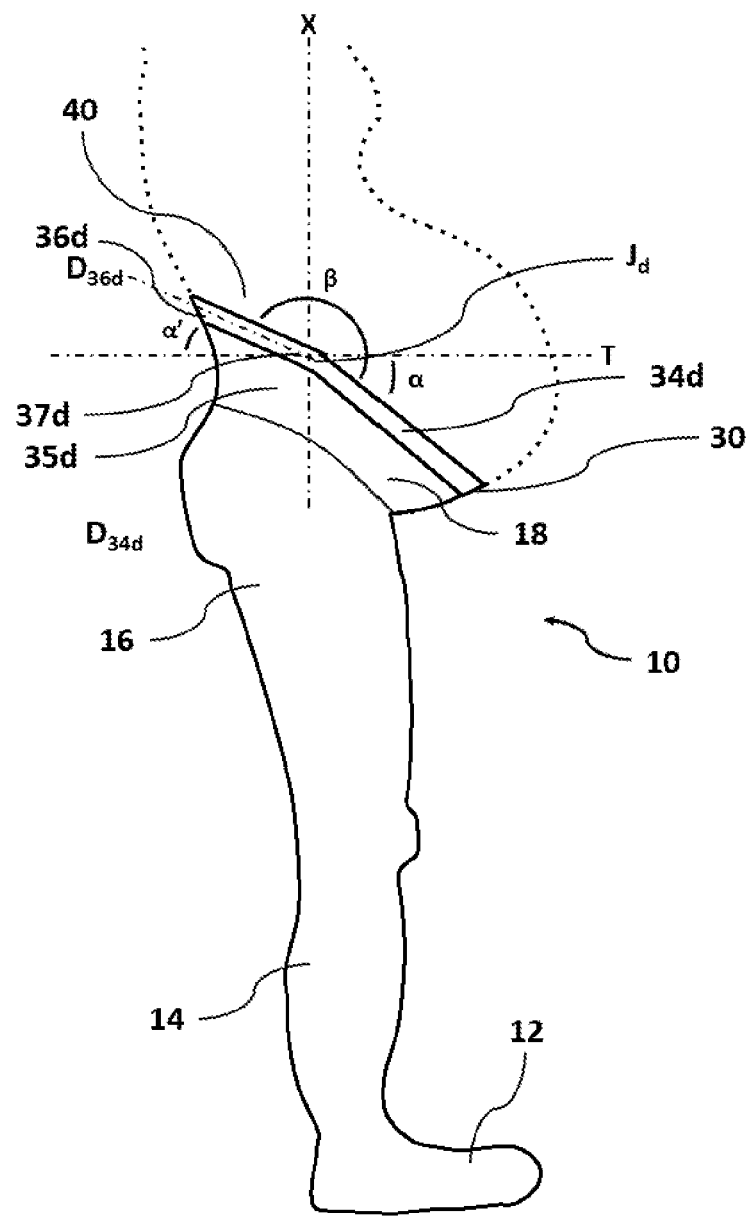

TEXTILE DEVICE FOR PREGNANT WOMEN

TECHNICAL FIELD

The present invention relates to a textile elastic venous compression device (or EVC device, hereinafter "device") specifically designed to treat venous disorders of the lower limbs of a pregnant woman.

PRIOR ART

An EVC device, also known as a "compression sock" when it extends up to the knee, or a "compression stocking" when it extends up to the thigh, or "compression tights" when it extends up to the waist, is a textile medical device that brings about a therapeutic effect by compressing the lower limbs, in contrast to "support" (or "anti-fatigue") stockings or tights and "fashion" stockings or tights.

The pressure profile exerted by the device usually decreases upwardly. To obtain such a profile, an EVC device is generally made from a knitted mesh with incorporation of an elastic weft thread, often a thread made of covered elastane.

The device is put on the lower limb(s) of the patient to be treated, as far as a use position. The return force of the elastic fibers then applies a pressure having a therapeutic effect.

In the case of a device of the tights type, extending up to the waist, only the part below the pelvis, or "panty part", is intended to exert therapeutic compression. The "panty part" is conventionally made as in non-medical tights. The panty part, which defines the opening by which the device is put on, conventionally has an elastic waistband that makes it possible, once the device has been put on, to keep it in position by locally exerting a holding pressure.

However, this waistband tends to move down when it sits on the protruding belly of a pregnant woman. Moreover, the pressure that it exerts on the belly may be very uncomfortable.

Devices of the tights type intended for pregnant women are therefore conventionally designed such that the waistband sits above the belly.

However, in this solution, the opening of the device is much less wide than the belly of the pregnant woman, making it difficult to put on.

Moreover, the pregnant woman may need to uncover her belly, without removing the device, in particular for reasons of thermal comfort or in order for an examination to be carried out, for example an ultrasound scan. This manipulation may also be difficult.

There is therefore a constant need for an EVC device designed for pregnant women that is comfortable, easy to put on and allows partial removal to uncover the belly.

An aim of the invention is to address this need, at least partially.

SUMMARY OF THE INVENTION

The invention provides a device intended for the treatment of a venous disorder of at least one lower limb of a pregnant woman, said device having:
- an elastic ventral band, preferably formed in one piece, having a right-hand ventral portion and a left-hand ventral portion that are intended to extend respectively on the right-hand side and the left-hand side of the pregnant woman's belly in a use position in which it is being worn by the pregnant woman, and
- preferably, a dorsal band, preferably formed in one piece, having a right-hand dorsal portion and a left-hand dorsal portion that are intended to extend respectively on the right-hand side and the left-hand side of the pregnant woman's back in said use position.

The device according to the invention is noteworthy in that, when it is viewed from a side view in said use position, that is to say in a "flat lateral position", the axis of at least one of the right-hand and left-hand ventral portions is inclined, with respect to a transverse plane, at an angle $\alpha$ greater than 5° and less than 80°.

As will be seen in more detail in the remainder of the description, the inclination of at least one, preferably of both ventral portions makes it possible to widen the opening of the device when it is being put on.

Furthermore, in the use position, the ventral portions may advantageously pass around the belly, while sitting on the belly. Therefore, they do not substantially compress the belly. The contact with the belly is also partially vertical. Holding in position is therefore possible with less elastic compression. This results in additional comfort for the pregnant woman.

Lastly, the inclination of the ventral portions makes it possible to flap them down in order to uncover the belly, without modifying the position of the rest of the waistband.

The device may comprise a ventral part, extending to above the belly of the pregnant woman, the ventral part comprising an elastic waistband, extensible mainly in the circumferential direction, the elastic waistband defining an opening through which the device is put on.

Preferably, the device is of class I, II, III or IV according to the ASQUAL standard. The device may be of class I, II, III and IV according to the RAL-GZ-387 standard.

A device according to the invention may also have one or more of the following optional and preferred features:
- said angle $\alpha$ is greater than 25° and less than 60°;
- the ventral band and/or the dorsal band do not have a vertical seam, and preferably do not have any seam;
- the left-hand dorsal portion and/or the right-hand dorsal portion is (are) designed such that, when the device is viewed from a side view in said use position, the axis of the left-hand dorsal portion and/or the axis of the right-hand dorsal portion, respectively, form(s) an angle $\beta$ greater than 90° and less than 150° with the axis of the left-hand ventral portion and/or with the axis of the right-hand ventral portion, respectively;
- the ventral and dorsal bands meet at a left-hand meeting point and a right-hand meeting point, in contact with the left-hand and right-hand sides of the pregnant woman in the use position;
- the ventral and dorsal bands are stitched together at said left-hand meeting point and right-hand meeting point;
- the ventral band extends above the dorsal band at said left-hand meeting point and right-hand meeting point;
- the right-hand ventral portion and left-hand ventral portion meet at a point and extend, on the opposite side from the point, beyond the right-hand meeting point and left-hand meeting point, respectively, along a length greater than 1 cm, 2 cm, 3 cm and/or less than 7 cm or 5 cm;
- the device has a fabric sheet for protecting the belly;
- the fabric sheet for protecting the belly is formed in one piece, preferably by knitting, and extends so as to pass around the pregnant woman in the use position;
- at least in the ventral part of the fabric sheet, that is to say the part which sits on the belly in the use position, the protective fabric sheet does not have a vertical seam, and preferably does not have any seam;

the device has two elastic ventral bands, known as the "upper ventral band" and "lower ventral band", the ends of the lower ventral band being connected to the upper ventral band such that the upper and lower ventral bands jointly encircle the pregnant woman's belly in the use position.

The elastic waistband of the ventral part can pass over the belly of the pregnant woman, in the use position. For example, the elastic ventral band of the elastic waistband may comprise at least one portion passing above the belly of the pregnant woman, in the use position.

The axis of said at least one of said right-hand ventral portion and left-hand ventral portion can be inclined downwards and towards the back of the pregnant woman, in the use position. In particular, the axis of the right-hand ventral portion of the elastic ventral band can be inclined downwards and towards the back of the pregnant woman. The axis of the left-hand ventral portion of the elastic ventral band can be inclined downwards and towards the back of the pregnant woman.

BRIEF DESCRIPTION OF THE FIGURES

Further features and advantages of the invention will become more apparent on reading the following detailed description, and on studying the drawing, in which FIG. 1 schematically shows, in the flat lateral position, a device according to the invention;

FIG. 2 schematically shows, in the use position, a front view of a device according to the invention;

FIG. 3 schematically shows, in the use position, a rear view of a device according to the invention;

FIG. 4 schematically shows, in the flat lateral position, a device according to the invention in another embodiment;

FIG. 5 schematically shows, in the flat lateral position, a device according to the invention in another embodiment.

DEFINITIONS

The "use position" of a device denotes the position in which it is used, meaning when it has been put on the lower limbs and the pelvis of a pregnant woman standing up, vertically.

The "ventral" and "dorsal" bands are bands that sit on the belly and on the back of the pregnant woman in the use position. They can be connected together, or only form a continuous strip, meeting at the right-hand and left-hand sides of the pregnant woman. Two parts of the ventral band are distinguished, namely the right-hand and left-hand ventral portions which extend, from the middle of the belly, respectively to the right and left of the belly. Two parts of the dorsal band are distinguished, namely the right-hand and left-hand dorsal portions which extend, from the middle of the back, respectively to the right and left of the back. Preferably, the ventral and dorsal bands meet on the right-hand and left-hand sides of the pregnant woman.

A band or a fabric sheet are "formed in one piece" when they do not have seams connecting multiple parts of said band or said fabric sheet. In other words, the band or the fabric sheet are formed exclusively by weaving or knitting.

The "rest" or "flat" position of a device is a position in which the device is laid flat on a flat surface. The device may in particular be disposed so as to be seen "in a front view" or "in a side view" or "in a rear view", that is to say along a viewing direction corresponding respectively to looking at the pregnant woman facing the pregnant woman, from the side and from the rear in the use position. When the device is flat and disposed so as to be seen in a side view, its position is a "flat lateral" position.

The adjectives "upper" and "lower" are used for clarity reasons, with reference to the vertical direction, in the use position.

The main axis X of the device is conventionally the direction in which the leg and panty parts thereof extend. It is used in particular to define heights or "levels" in the standard NF_S_97_114. The main axis is therefore vertical in the use position. A transverse plane is a plane perpendicular to the main axis of the device.

A "mesh" is a loop of knitting threads.

Unless indicated otherwise, the verbs "have", "comprise" or "include", and any expression denoting inclusion, should be interpreted as being non-exclusive.

DETAILED DESCRIPTION

Device

The reference 10, shown in FIG. 1, generally denotes a device according to the invention.

The device 10, of anatomical overall shape, comprises, successively from the end of the foot:

optionally a foot part 12 which envelops the foot, extending from the toes to the ankles, covering the instep;

a leg part 14, able to be stretched in a longitudinal direction (that is to say along the main direction X) and in a circumferential direction (radial stretchability), which extends in the continuation of the foot part 12, up to a level situated above the knee;

a panty part 16, also able to be stretched in longitudinal and circumferential directions, extending in the continuation of the leg part 14, as far as the waist of the pregnant woman; and a belly part 18, extending in the continuation of the panty part 16 to above the belly of the pregnant woman;

the belly part 18 having an elastic waistband 30, able to be stretched mainly in the circumferential direction, the waistband 30 defining an opening 40 via which the device is put on.

The device 10 comprises tights made up of the foot, leg and panty parts. The tights cover the two lower limbs and extend up to the waist when the device is in the use position.

The tights may have all the features of prior art tights commonly used to treat venous insufficiency. The nature of the threads and the stitches used are adapted depending on the therapeutic action and the appearance that are desired for the various parts of the device. This adaptation is not particularly difficult for a person skilled in the art.

The device 10 is conventionally produced from a knitted mesh and incorporates, in the leg part, an elastic weft thread, generally made of a covered elastane. Preferably, it is knitted in one piece.

In different embodiments of the invention, the knitting can be carried out such that the compression is limited to the areas situated below the knee, or such that it extends above the knee. Similarly, in different embodiments, the knitting can be carried out such that the therapeutic compression affects only one lower limb. Preferably, it affects both lower limbs.

The pressure profile exerted by the tights preferably decreases upwardly from the ankle.

Depending on the type of device, the pressure measured at the ankle may in particular vary from 10 to more than 36 mmHg (or 13 to 48 hPa, mmHg being commonly used, however, as a pressure measurement unit in the field of phlebology and of medical compression).

The devices are classified according to the ASQUAL standard into four textile classes, from class I (13 to 20 hPa≈10 to 15 mmHg at the ankle) to class IV (>48 hPa≈>36 mmHg at the ankle).

Preferably, the device is of class I, II, III or IV according to the ASQUAL standard, or of class I, II, III and IV according to the RAL-GZ-387 standard, preferably of class II according to the ASQUAL standard.

The tights may have the same external appearance as "fashion" tights.

The belly part 18 is specific to the devices intended for pregnant women. It is not intended to have a therapeutic effect, but rather to keep the tights in the particular configuration of the belly of a pregnant woman. In the absence of a belly part, the belly of the pregnant woman tends to push the tights down, impairing their effectiveness and comfort.

In one embodiment, it has a fabric sheet 20, preferably knitted, designed to partially or entirely cover the belly in the use position. It extends between the panty part of the device and the ventral and dorsal bands.

Such a fabric sheet is involved in the thermal and mechanical protection of the belly. It may also improve comfort, in particular by limiting friction between the skin and the waistband 30.

Preferably, the fabric sheet 20 is designed not to exert pressure on the belly. Preferably, it is made from the same material and/or with the same mesh as the panty part. Preferably, it is knitted together with the panty part.

Preferably, the fabric sheet 20 encircles the device, meaning that it extends so as to pass around the pregnant woman in the use position.

Preferably, it is formed in one piece, preferably by knitting, for example with a jersey mesh.

Preferably, at least in the part that sits on the belly in the use position, the fabric sheet 20 does not have a vertical seam, and preferably does not have any seam. In a preferred embodiment, it has only one seam, preferably a vertical seam which, in the use position, extends at the middle of the back. This improves comfort.

Preferably, its height, measured along the axis X of the device, is greater in the ventral part of the device, that is to say in the region in which the fabric sheet covers the belly in the use position.

In one embodiment, as illustrated in FIG. 4, in particular when the device is intended to be used in the summer, the fabric sheet 20 may be absent. The device then does not have any material between the ventral band and the panty part.

The function of the waistband 30 is to fit elastically on the pregnant woman so as to keep the device in the use position, to prevent it from dropping. It is preferably disposed at the upper end of the device.

The dimensions and the structure of the waistband are adapted to the desired hold. This adaptation is not difficult for a person skilled in the art. Preferably, the waistband 30 is an attached elastic band.

In one embodiment, the only difference between the panty part or the fabric sheet 20 and the waistband resides in the mesh.

Preferably, the count of the core of the mesh thread of the waistband is less than 44 dTex, preferably less than 30 dTex, preferably less than 25 dTex, preferably less than 20 dTex, and/or greater than 10 dTex, preferably greater than 15 dTex.

Preferably, the count of the covering thread of the mesh thread of the elastic waistband is less than 60 dTex, preferably less than 50 dTex, preferably less than 45 dTex, and/or greater than 20 dTex, preferably greater than 30 dTex, preferably greater than 40 dTex.

Preferably, the weft thread of the elastic waistband is a covered thread, preferably a double-covered thread.

Preferably, the count of the core of the weft thread of the waistband is less than 150 dTex, preferably less than 140 dTex, preferably less than 135 dTex, and/or greater than 100 dTex, preferably greater than 110 dTex, preferably greater than 120 dTex, preferably greater than 125 dTex.

Preferably, the count of the covering thread of the weft thread of the waistband is less than 40 dTex, preferably less than 30 dTex, preferably less than 25 dTex, and/or greater than 10 dTex, preferably greater than 15 dTex, preferably greater than 20 dTex.

The waistband 30 is disposed so as to extend, in the use position, at least partially above the belly, preferably following the contour of the belly. Preferably, the waistband 30 extends, in the use position, through at least 360° around the pregnant woman, preferably through less than 450°. It has:

- a ventral band 34, which extends, in the use position, in front of the pregnant woman, from a left-hand "ventral" end 35g and a right-hand "ventral" end 35d, and preferably
- a dorsal band 36, which extends, in the use position, behind the pregnant woman, from a left-hand "dorsal" end 37g and a right-hand "dorsal" end 37d.

Preferably, the ventral band and/or the dorsal band is (are) symmetric with respect to the median sagittal plane S, in the use position.

The elastic properties of the ventral and dorsal bands are preferably identical, but may be different. Preferably, at least the ventral band 34 is elastic. Preferably, the waistband 30 is elastic along its entire length.

The ventral and dorsal bands may form a common band, the ventral band being just the continuation of the dorsal band, and vice versa. Preferably, however, they form two distinct, i.e. independent, bands. Advantageously, any movement of the ventral band has little impact on the position of the dorsal band. The two distinct bands may be connected to one another, preferably by means of connecting seams.

Preferably, away from these connecting seams, the ventral band and/or the dorsal band do not have a vertical seam, and preferably do not have any seam. In other words, they are each formed in one piece. This improves comfort.

Preferably, the ventral and dorsal bands form two distinct bands, the ventral and dorsal bands meeting on the left-hand side of the pregnant woman at a left-hand meeting point $J_g$, preferably being stitched together, and on the right-hand side of the pregnant woman at a right-hand meeting point $J_d$, preferably being stitched together.

Preferably, at said meeting points, the ventral band is stitched on top of the dorsal band.

Preferably, the ventral band 34 and dorsal band 36 form, at their right-hand ends and/or at their left-hand ends, an angle β greater than 100°, 110°, 120°, or 130°, and preferably less than 170°, 160° or 150°.

In a position in which the waistband is put on a cylinder of circular section dimensioned so that the waistband fits on this cylinder, but without substantially compressing it, the length of the waistband 30, through 360° around the cylinder, is then greater than the perimeter of the base circle of this cylinder. The ratio of this length to this perimeter is preferably greater than 105%, 110%, 120% and/or less than 180%.

Advantageously, the putting on and removal of the device through the opening 40 are thus much easier.

In a preferred embodiment, as shown in the figures, the ventral band 34 and/or the dorsal band 36 are rectilinear, meaning that a pull on their ends allows them to be aligned along a straight line. In other words, before being incorporated in the device, the ventral band 34 and/or the dorsal band 36 formed a straight ribbon.

The width $l_{34}$ of the ventral band 34 may be identical to or different than the width of the dorsal band 36. The width $l_{34}$ of the ventral band 34 is preferably greater than 0.5 cm, 1 cm, 2 cm or 3 cm and/or less than 10 cm, 8 cm, 6 cm or 5 cm.

The thickness of the ventral band 34 and/or of the dorsal band 36 is preferably substantially identical to that of the fabric sheet 20, and preferably substantially identical to that of the panty part.

The ventral band 34 has, and is preferably made up of a right-hand ventral portion 34d and a left-hand ventral portion 34g, which are intended to extend respectively on the right-hand side and the left-hand side of the belly of the pregnant woman in the use position, as far as her sides. The right-hand ventral portion 34d and left-hand ventral portion 34g are therefore visible when the device is in right-hand (FIG. 1) and left-hand flat lateral positions, respectively.

They meet at the middle $M_{34}$ of the ventral band, in the median sagittal plane, and extend respectively as far as the right-hand end 35d and left-hand end 35g, respectively. Preferably, the right-hand ventral portion 34d and/or left-hand ventral portion 34g extend, on the opposite side from the middle $M_{34}$, beyond a right-hand meeting point $J_d$ and a left-hand meeting point $J_g$. The distance between the right-hand end 35d and left-hand end 35g and the right-hand meeting point $J_d$ and left-hand meeting point $J_g$, respectively, may be greater than 1 cm, 2 cm, 3 cm and/or less than 7 cm or 5 cm. Preferably, this distance is zero, this advantageously limiting the occurrence of folds when, in the use position, the woman uncovers her belly by lowering the fabric sheet 20, and increasing the lifetime of the device.

In one embodiment, the ventral band passes over the dorsal band at said left-hand meeting point $J_g$ and right-hand meeting point $J_d$, preferably without being stitched to the dorsal band. The independence of the ventral band with respect to the dorsal band is further improved thereby.

Preferably, the ventral band is fixed, preferably stitched, to the panty part or to the fabric sheet 20, at its right-hand end 35d and left-hand end 35g. This increases comfort.

The right-hand ventral portion 34d and left-hand ventral portion 34g are preferably symmetric with respect to the median sagittal plane S. Therefore, only the right-hand ventral portion 34d is described in detail below, with reference to the right-hand flat lateral position.

The designation "axis" $D_{34d}$ of the right-hand ventral portion 34d is given to the straight line which, in the right-hand flat lateral position (FIG. 1), connects the middle $M_{34}$ of the ventral band and the right-hand end 35d. Preferably, the right-hand ventral portion 34d is substantially rectilinear and therefore extends along the axis $D_{34d}$. The right-hand ventral portion 34d may also have a curve, in particular to better follow the contour of the pregnant woman's belly.

According to the invention, the axis $D_{34d}$ forms, with a transverse plane T, an angle α greater than 5°, preferably greater than 10°, 15°, 20°, 25°, 35° or 45°, and preferably less than 80°, 70° or 60°. In the use position, the right-hand ventral portion 34d is therefore inclined with respect to a horizontal plane. An angle α of between 45° and 60° is considered to be optimal.

This configuration advantageously allows the waistband to pass around the belly, thereby making it possible to reduce the pressure exerted on the belly.

It also allows a particularly low meeting point with the dorsal portion, making it easier to uncover the belly of the pregnant woman, from the use position. Preferably, the difference in height, measured along the axis X of the device, between the right-hand end 35d of the right-hand ventral portion 34d and the middle $M_{34}$ is greater than 5 cm, 7 cm or 10 cm and/or less than 30 cm.

The inclination also makes it possible to substantially follow the folds of the skin, thereby making the device particularly comfortable and limiting the risks of irritation by friction against the skin.

In one embodiment, as illustrated in FIG. 4, in particular in the absence of a fabric sheet 20, the device preferably has a second ventral band configured to pass underneath the belly. This improves comfort. Preferably, the second ventral band, or "lower ventral band", meets the first ventral band, or "upper ventral band", at its two ends. The belly is thus encircled in the use position. The lower ventral band may be identical to or different than the upper ventral band.

The dorsal band 36 has, and is preferably made up of a right-hand dorsal portion 36d and a left-hand dorsal portion 36g, which are intended to extend respectively on the right-hand side and the left-hand side of the median sagittal plane S. The right-hand dorsal portion 36d and left-hand dorsal portion 36g are therefore visible when the device is in right-hand (FIG. 1) and left-hand flat lateral positions, respectively.

They meet at the middle $M_{36}$ of the dorsal band, in the median sagittal plane, and extend respectively as far as the right-hand end 37d and left-hand end 37g, respectively.

The difference in height between the middles $M_{34}$ and $M_{36}$, measured along the main axis X of the device, is preferably greater than 2 cm, 3 cm, 4 cm and/or less than 15 cm, or 10 cm.

The right-hand dorsal portion 36d and left-hand dorsal portion 36g are preferably symmetric with respect to the median sagittal plane S. Therefore, only the right-hand dorsal portion 36d is described in detail below, with reference to the right-hand flat lateral position.

The designation "axis" $D_{36d}$ of the right-hand dorsal portion 36d is given to the straight line which, in the right-hand flat lateral position (FIG. 1), connects the middle $M_{36}$ of the dorsal band and the right-hand end 37d. Preferably, the right-hand dorsal portion 36d is substantially rectilinear and therefore extends along the axis $D_{36d}$.

Preferably, the axis $D_{36d}$ forms, with a transverse plane T, an angle α' that is preferably smaller than the angle α. Preferably, the angle α' is greater than 5°, preferably greater than 5°, 10°, 15°, or 20°, and preferably less than 80°, 70°, 60°, 50°, 30°. In the use position, the right-hand dorsal portion 36d is therefore inclined with respect to a horizontal plane. An angle α' of between 20° and 30° is considered to be optimal.

The inclination of the dorsal band likewise improves comfort. Furthermore, it makes it possible to reduce the angle β, and thus to increase the independence of movement between the ventral and dorsal bands. The belly can thus be uncovered without this action modifying the position of the dorsal band.

Functioning

The functioning of the device follows directly from the above text.

To put it on, the pregnant woman widens the opening 40 by pulling on the waistband. The inclination of the ventral and dorsal bands allows this opening to be widened greatly without effort. It makes it easier to put it on, but also to pass over the belly.

After this passage has taken place, the pregnant woman positions the waistband correctly, in particular in order that the ventral band extends around the upper part of her belly. The ventral band then rests at least partially on the belly and the belly prevents any lowering of the device. The ventral band does not substantially compress the belly, however.

When the pregnant woman wishes to uncover her belly, she elastically spreads the ventral band and lowers it. The drop-off at the meeting points between the ventral and dorsal bands makes it easier to rotate about these points. The movement of the ventral band therefore does not affect, or affects only to a limited extent, the dorsal band, which therefore continues to effectively support the device.

Finally, when the pregnant woman bends laterally, the orientation of the waistband, and in particular of the ventral band, substantially follows the folds of the skin, thereby further contributing to comfort.

As will now be clearly apparent, a device according to the invention may be put on easily, does not substantially compress the belly, can be held in position effectively and with limited contact pressure of the waistband, and allows the belly to be uncovered easily.

Of course, the invention is not limited to the embodiments described and depicted, these being provided only for illustrative purposes.

In particular, the elastic waistband may not include an elastic dorsal band, although the presence of the latter constitutes a preferred embodiment.

The invention claimed is:

1. Device for the treatment of a venous disorder of at least one lower limb of a pregnant woman, said device having:
    a leg part able to be stretched in a longitudinal direction and in a circumferential direction, wherein the leg part is configured to extend from a foot of the pregnant woman up to a level situated above a knee of the at least one lower limb,
    an elastic ventral band having a right-hand ventral portion and a left-hand ventral portion that are configured to extend respectively on a right-hand side and a left-hand side of the pregnant woman's belly in a use position in which said device is being worn by the pregnant woman, and
    a dorsal band having a right-hand dorsal portion and a left-hand dorsal portion that are configured to extend respectively on a right-hand side and a left-hand side of the pregnant woman's back in said use position,
    wherein, when the device is viewed from a side view in said use position, the axis of at least one of the right-hand and left-hand ventral portions is inclined, with respect to a transverse plane, at an angle greater than 5° and less than 80°, a transverse plane being a plane perpendicular to the main axis X of the device, and
    wherein the dorsal band forms a straight ribbon.

2. Device according to claim 1, wherein said angle is greater than 25° and less than 60°.

3. Device according to claim 1, wherein the left-hand dorsal portion and/or the right-hand dorsal portion is (are) designed such that, when the device is viewed from a side view in said use position, the axis of the left-hand dorsal portion and/or the axis of the right-hand dorsal portion, respectively, form(s) an angle β greater than 90° and less than 150° with the axis of the left-hand ventral portion and/or with the axis of the right-hand ventral portion, respectively.

4. Device according to claim 1, wherein the ventral and dorsal bands meet at a left-hand meeting point and a right-hand meeting point, in contact with the left-hand and right-hand sides of the pregnant woman in the use position.

5. Device according to claim 4, wherein the ventral and dorsal bands are stitched together at said left-hand meeting point and right-hand meeting point.

6. Device according to claim 5, wherein the ventral band extends above the dorsal band at said left-hand meeting point and right-hand meeting point.

7. Device according to claim 4, wherein the right-hand ventral portion and left-hand ventral portion meet at a point and extend, on the opposite side from the point, beyond the right-hand meeting point and left-hand meeting point, respectively, along a length greater than 1 cm.

8. Device according to claim 4, wherein the right-hand ventral portion and left-hand ventral portion meet at a point and extend, on the opposite side from the point, beyond the right-hand meeting point and left-hand meeting point, respectively, along a length less than 7 cm.

9. Device according to claim 1, having a fabric sheet for protecting the belly.

10. Device according to claim 9, wherein the fabric sheet is configured to pass around the pregnant woman in the use position.

11. Device according to claim 9, wherein at least a ventral part of the protective fabric sheet does not have a seam.

12. Device according to claim 1, wherein the ventral band and/or the dorsal band do not have a seam.

13. Device according to claim 1, wherein the elastic ventral band comprises an upper ventral band and a lower ventral band, ends of the lower ventral band being connected to the upper ventral band such that the upper and lower ventral bands jointly encircle the pregnant woman's belly in the use position.

14. Device according to claim 1, wherein the device is configured to provide an amount of pressure measured at the ankle between 10 to 36 mmHg.

* * * * *